(12) United States Patent
Jalde

(10) Patent No.: US 8,280,498 B2
(45) Date of Patent: Oct. 2, 2012

(54) METHOD, VENTILATOR AND CONTROL UNIT FOR DETERMINING A POSITION OF AN ESOPHAGEAL CATHETER

(75) Inventor: Fredrik Jalde, Bromma (SE)

(73) Assignee: Maquet Critical Care AB, Solna (SE)

( * ) Notice: Subject to any disclaimer, the term of this patent is extended or adjusted under 35 U.S.C. 154(b) by 420 days.

(21) Appl. No.: 12/615,405

(22) Filed: Nov. 10, 2009

(65) Prior Publication Data

US 2010/0116274 A1  May 13, 2010

(30) Foreign Application Priority Data

Nov. 13, 2008 (SE) ........................ 0850076

(51) Int. Cl.
*A61B 5/04* (2006.01)

(52) U.S. Cl. ...................................... 600/509

(58) Field of Classification Search .................. 600/380, 600/509, 350, 424, 425; 607/40, 124, 133
See application file for complete search history.

(56) References Cited

U.S. PATENT DOCUMENTS

| | | | |
|---|---|---|---|
| 5,431,696 A * | 7/1995 | Atlee, III | 607/124 |
| 5,671,752 A | 9/1997 | Sinderby et al. | |
| 5,749,833 A * | 5/1998 | Hakki et al. | 600/380 |
| 5,820,560 A | 10/1998 | Sinderby et al. | |
| 6,588,423 B1 | 7/2003 | Sinderby | |
| 6,651,652 B1 | 11/2003 | Wārd | |
| 2009/0084382 A1 | 4/2009 | Jalde et al. | |

* cited by examiner

*Primary Examiner* — George Evanisko
*Assistant Examiner* — Christopher A Flory
(74) *Attorney, Agent, or Firm* — Schiff Hardin LLP

(57) ABSTRACT

A method of obtaining an indication of the position of an esophageal catheter inserted into a patient includes the steps of obtaining an electrical signal from the esophageal catheter, determining an ECG component of the electrical signal, determining the widths and/or rate of a number of periods in which the ECG component exceeds a threshold value, using the rate or widths of the periods to determine the presence of a P-wave in the ECG component, and concluding that the catheter is in a good position for obtaining a correct EMG signal if a P-wave is determined to be present. If not, the position may be corrected. The method may be performed by a control unit in a ventilator or a monitoring device.

15 Claims, 4 Drawing Sheets

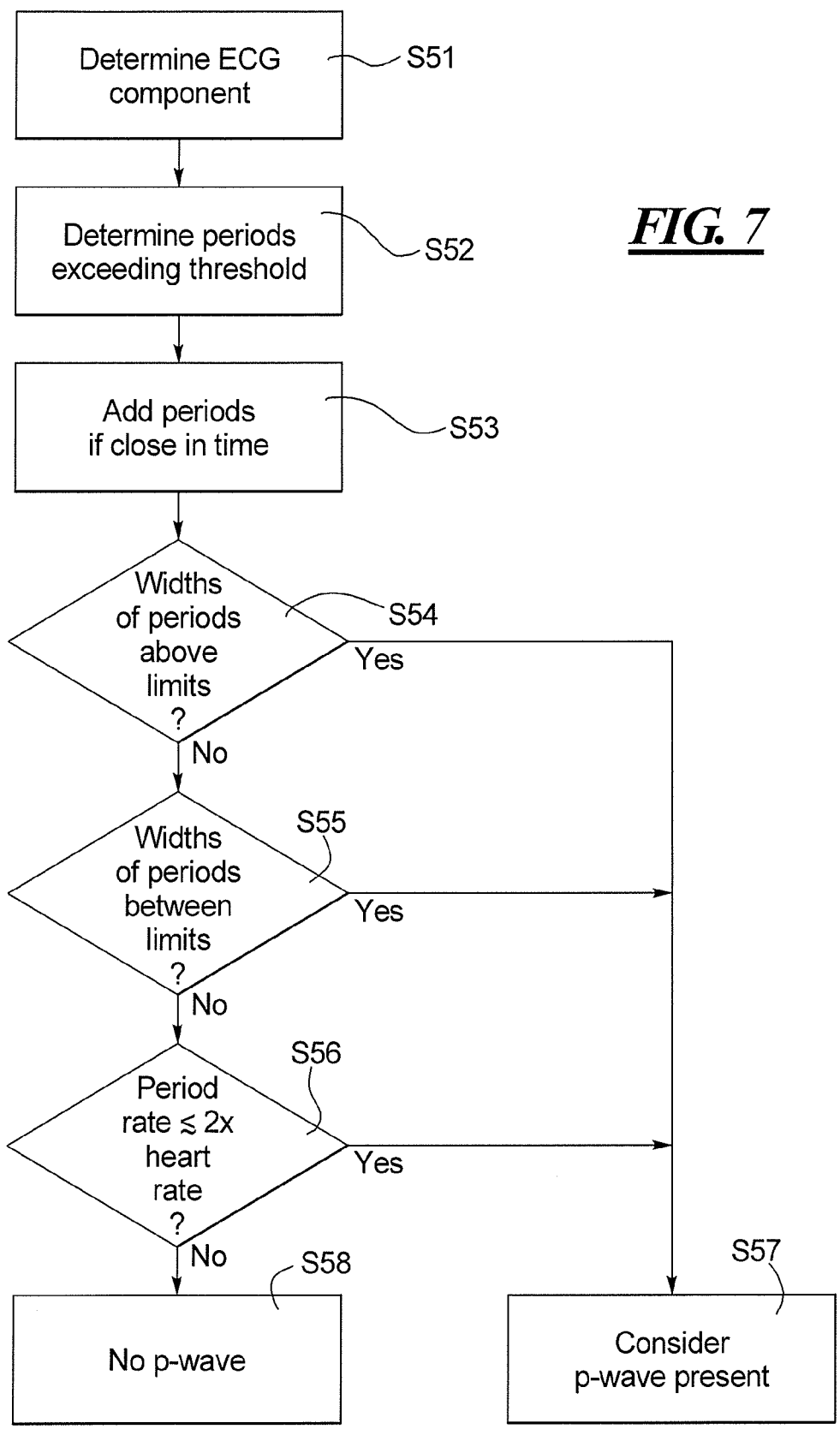

METHOD, VENTILATOR AND CONTROL UNIT FOR DETERMINING A POSITION OF AN ESOPHAGEAL CATHETER

BACKGROUND OF THE INVENTION

1. Field of the Invention

The present invention relates to a method of determining the position of a catheter in a patient's esophagus, a control unit for controlling the monitoring of an electric signal from a catheter in a patient's esophagus, and a computer program product for use in such a control unit.

2. Description of the Prior Art

It is known in the art to use myoelectrical signals from a patient to control the function of a ventilator providing breathing support to the patient. U.S. Pat. Nos. 5,820,560 and 6,588,423 both disclose methods and devices for triggering ventilatory support to a patient using a myoelectrical signal obtained from the diaphragm. U.S. Pat. No. 5,671,752 discloses a method and a device for registering the myoelectrical activity of the diaphragm by means of an esophageal catheter having an array of electrodes. The signals from such a catheter can be used as the myoelectrical signal to control ventilator function. EP 1 091 780 discloses the use of a neuroelectrical signal picked up, for example, from the phrenic nerve to control a ventilator.

A problem when obtaining a myoelectrical signal from the diaphragm is positioning of the catheter within the patient's esophagus. To obtain a proper signal some of the electrodes of the catheter should be placed above the diaphragm and some below it. There is a possibility that the catheter will be inserted too far, or not be inserted far enough. In both cases, the catheter will detect a weak signal, or may not capture any signal at all. Alternatively, the catheter may capture myoelectrical signals from other muscles instead of, or in addition to the signal from the diaphragm. Hence, it is difficult to obtain an optimal catheter position and the ventilator may have to work in pneumatic triggering mode if the signal is too weak.

Co-pending Swedish Application No. SE 0702191-8 discloses a method of positioning the catheter based on the ECG component that will always be present in a myoelectrical signal from the diaphragm. In this application, the damping of the ECG signal caused by the diaphragm is used. The ECG signal components from different electrode pairs are determined and compared and the difference in amplitude of the ECG signal between different electrode pairs is used to determine the position of the diaphragm relative to the electrode pairs. The greatest damping between two neighboring electrode pairs should be caused by the diaphragm being positioned between these two electrode pairs. This method is predominantly based on the registration and comparison of the QRS complex of the ECG signal.

SUMMARY OF THE INVENTION

An object of the invention is to ascertain correct placement of an esophageal catheter in a patient.

This object is achieved in accordance with the invention by a method of obtaining an indication of the position of an esophageal catheter inserted into a patient, the method including the steps of obtaining an electrical signal from the esophageal catheter, determining an ECG component of the electrical signal, determining the widths and/or rate of a number of periods in which the ECG component exceeds a threshold value, using the rate or widths of the periods to determine the presence of a P-wave in the ECG component, concluding that the catheter is in a good position for obtaining a correct EMG signal if a P-wave is determined to be present.

The object is also achieved by a computer-readable medium encoded with programming instructions which, when run in a processor, will cause the processor to process an EMG signal to determine an ECG component of the EMG signal, determine the widths of a number of periods in which the ECG component exceeds a threshold value, use the widths and/or rates of the periods to determine the presence of a P-wave in the ECG component, and conclude that the catheter is in a good position for obtaining a correct EMG signal if a P-wave is determined to be present.

The object is also achieved by a control unit for controlling a device that monitors an EMG signal, the control unit being configured to process the EMG signal to determine an ECG component of the EMG signal, determine the widths of a number of periods in which the ECG component exceeds a threshold value, use the widths of the periods to determine the presence of a P-wave in the ECG component, conclude that the catheter is in a good position for obtaining a correct EMG signal if a P-wave is determined to be present.

This solution makes use of the fact that the P-wave is usually detectable near the atria of the heart but not by electrodes that are farther down in the esophagus.

If the P-wave is detectable in the signal detected by an electrode pair, this is a strong indication that this electrode pair is located above the diaphragm. The method enables continuous monitoring of the catheter's position with a reasonable degree of accuracy. In the prior art, detection of the P-wave is generally performed by an operator looking at the curves.

The presence of a P-wave may be determined by using the widths of the periods to determine the presence of a P-wave close to a QRS complex. If a P-wave occurs close to a QRS complex the P-wave and QRS complex may be treated together as one period, which will then be longer than the period of the normal QRS complex. In particular, it may be determined that a P-wave is present if one of the two most frequent period widths exceeds a certain limit value, representing a width that is longer than the period of the normal QRS complex.

Alternatively, or in addition to the above, it may be determined that a P-wave is pre-sent if more than a certain fraction of the period widths are between a lower and an upper limit value. In this case, the period widths may be distributed over several values within an interval defined by the upper and lower limit value. The upper and lower limit values should be defined in such a way that the period widths falling within the interval are representative of a combined P-wave and QRS complex.

Alternatively, or in addition to the above, the rate of the periods, and the heart rate, may be determined. The rate of the periods is then compared to the heart rate, and it is determined that a P-wave is present if the rate of the periods is close to twice the heart rate. In this case a P-wave is considered to be present at almost every heart beat, separated in time from the QRS complex by more than the certain limit value.

If no P-wave is determined to be present, it should be determined if the catheter is in a bad position. This may be done in different ways, for example, by checking the NEX value.

The computer program may also cause the control unit to present the determined position of the catheter to the user on a display, for example, the display of the ventilator. This will assist the operator in determining the position of the catheter correctly.

The invention also relates to a monitoring device for monitoring an electrical signal from an esophageal catheter and having a control unit according to the above. The monitoring device may be a ventilator for providing breathing support to a patient, and further arranged to monitor an electrical signal obtained from an esophageal catheter inserted into the patient, the ventilator having a control unit as defined above.

BRIEF DESCRIPTION OF THE DRAWINGS

FIG. 7 is a flow chart of an overall process in accordance with the invention.

DESCRIPTION OF THE PREFERRED EMBODIMENTS

Figure 1A:
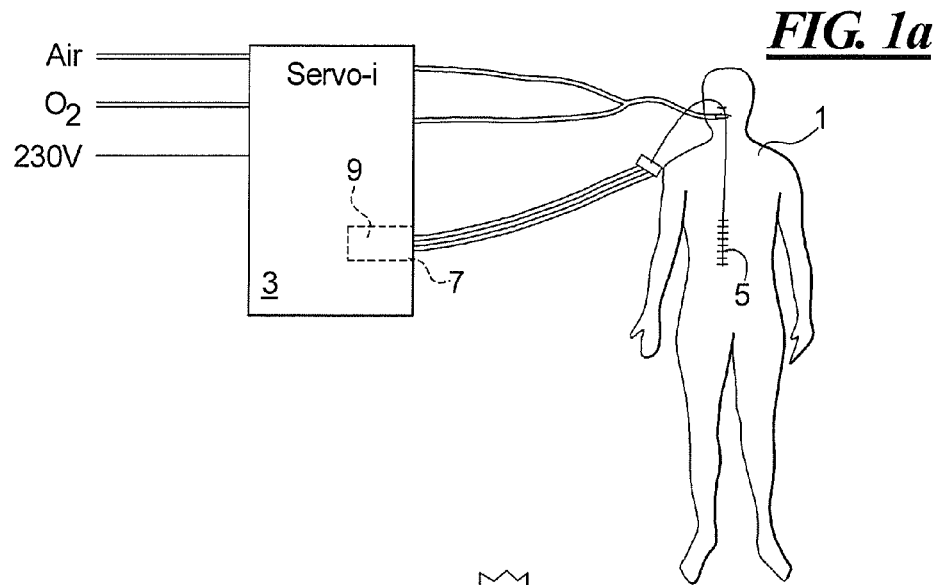
FIG. 1a illustrates a patient connected to a breathing support apparatus that may be used according to the invention.

FIG. 1a is a schematic overview of a patient 1 connected to a ventilator 3 and having an esophageal catheter 5 inserted in order to record a myoelectric signal from the diaphragm. This myoelectric signal is fed to a control input 7 of the ventilator 3 to control the ventilation function of the patient 1. The catheter 5 has a number of electrodes, for example, nine electrodes placed equidistantly in an array along the catheter to produce 8 subsignals, each subsignal being a difference signal between two neighboring electrodes. The subsignals will be processed in a control unit 9 in the ventilator to produce the overall signal that can be used to control the ventilator. To this end, the control unit 9 has at least one computer-readable medium used to control the ventilator to perform the calculations and other relevant functions.

Figure 1B:
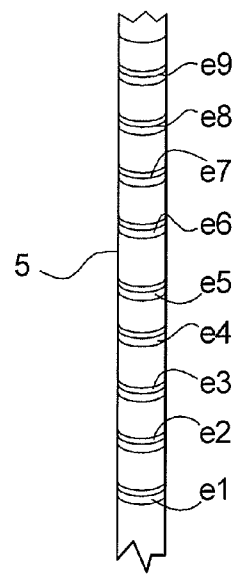
FIG. 1b shows an example of an esophageal catheter.

FIG. 1b shows a schematic example of an esophageal catheter 5 like the one shown in FIG. 1a. The catheter has nine electrodes, numbered e1, e2, . . . , e9 in the Figure. Each channel is recorded as the difference signal between two adjacent electrodes, that is, between e1 and e2, between e2 and e3, etc. Hence, the uppermost channel will be the one recorded between the two uppermost electrodes e8 and e9, also referred to as the uppermost electrode pair.

The registration of a myoelectric (EMG) signal from the diaphragm may not always be successful. As for any bioelectric signal, the EMG signal recorded from the diaphragm will comprise disturbance, in particular the ECG signal from the heart, but also from other muscles such as abdominal muscles. If the catheter is inserted much too far into the patient, the disturbing signals may constitute the largest part of the signal picked up by some or all the electrode pairs. In this case, there is a risk that the control signal provided to the ventilator is not related to the patient's breathing activity. In other cases, the patient may exhibit no breathing activity, or too little breathing activity to enable a proper registration.

Ensuring the correct positioning of the catheter within the patient is therefore important. Some methods for approximating how far the catheter should be inserted are known. For example the Xiphoid process involves measuring the distance between the bridge of the nose and the earlobe. Based on this distance the distance from the mouth or nose to the esophagogastric junction can be estimated. This is often referred to as NEX, or Nose to ear Xiphoidus measurements. This estimated distance can be used as an initial value when positioning the catheter in the esophagus of a patient. This is, however, only an estimate which may be more or less accurate depending on individual variations. This is discussed in the Journal of Advanced Nursing 2007 August; 59(3):274-289. For small children, and especially for premature babies, the distance may be estimated by measuring the circumference of the head. Such a method is disclosed, for example, in WO 2005/115234.

Even if the catheter is initially positioned in the right place it may be moved up or down within the patient's esophagus because of the patient's breathing activity or other movements, so that after a while the diaphragm activity is not registered in the right way.

According to an aspect of the invention detection of the P-wave of the ECG may be used as an indicator of whether the catheter is in the right place.

Figure 2:
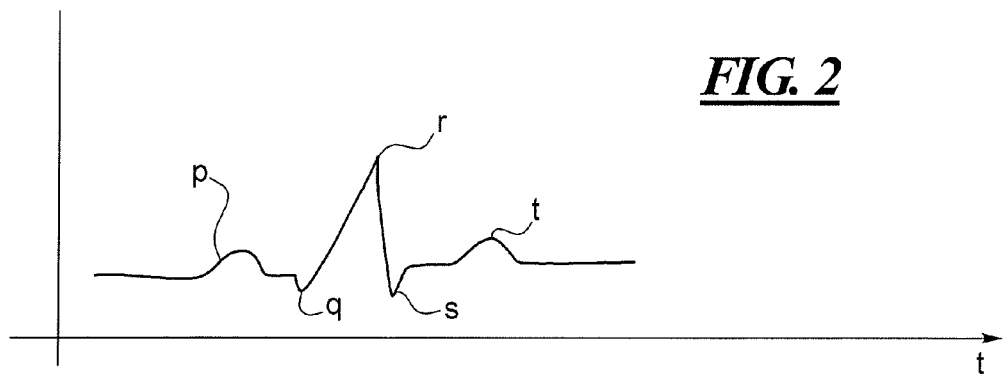
FIG. 2 illustrates a typical ECG signal.

FIG. 2 illustrates a typical ECG signal from one single heart beat. The signal starts with a P-wave, corresponding to the depolarization of the heart's atria. The QRS complex indicates the depolarization of the ventricles and is followed by the T wave which indicates the repolarization of the ventricles. According to the present invention the presence of the P-wave in the ECG signal captured by some of the electrodes of the catheter is used as an indicator that the catheter is correctly placed. In particular, at least some of the uppermost electrodes should detect a P-wave. If this is the case, it can be concluded that the catheter is not in the stomach and is not placed too high in the patient's esophagus.

Figure 3A:
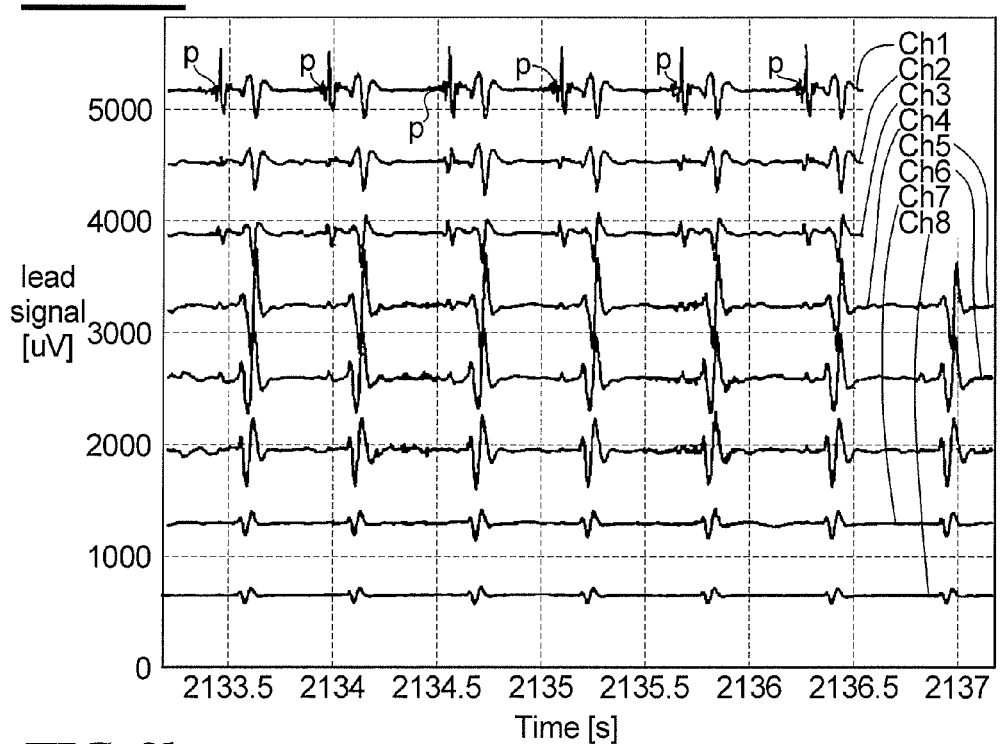
FIGS. 3a and 3b show examples of the difference between the ECG component when the catheter is in a good position and when it has been inserted too far, respectively.

FIG. 3a shows an example of the ECG component for each of the 8 electrode pairs when the catheter is in a good position. The position is considered to be good if the uppermost channel, resulting from the uppermost electrode pair in the patient, detects the P-wave. This indicates that the channels received from the middle electrode pairs of the catheter are probably in a good position for picking up the myoelectric signal from the diaphragm. As can be seen, in the example, the three uppermost electrode pairs have a clearly visible P-wave, marked with the letter p in the Figure, indicating a good position of the catheter. For the electrode pairs that are inserted further into the patient, the P-wave gradually decreases and becomes invisible.

Figure 3B:
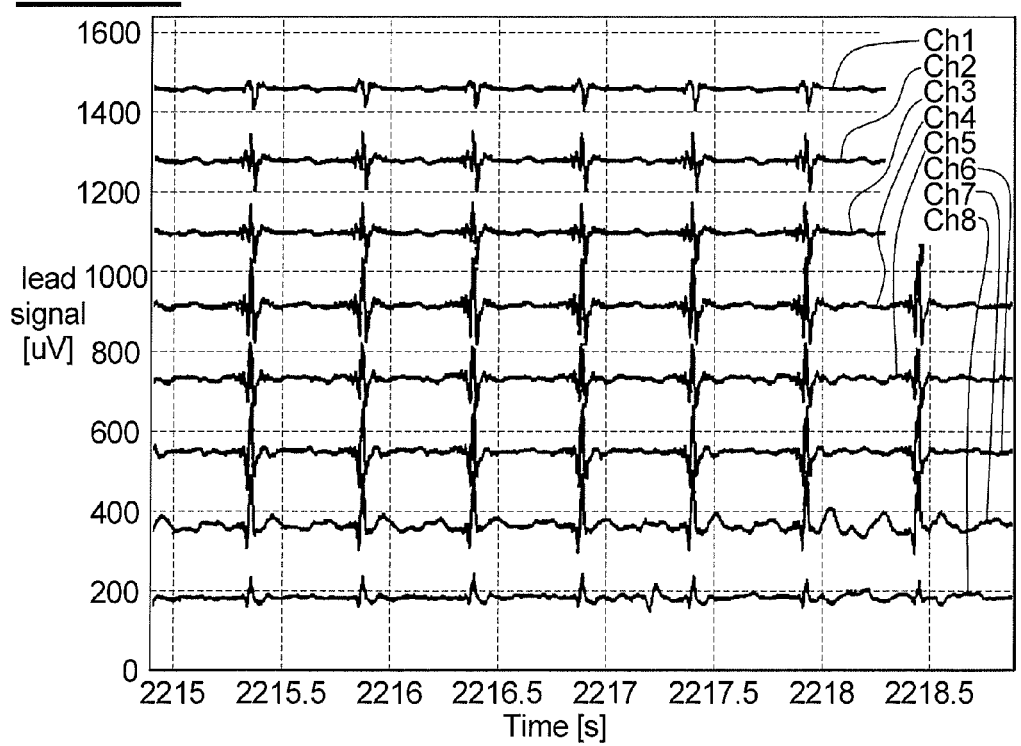

FIG. 3b shows an example of the ECG component for each of the 8 electrode pairs when the catheter is inserted too far into the patient. None of the 8 signals display a significant P-wave.

The presence of a P-wave may be detected by a number of different methods, as will be discussed in more detail in the following. Some of these methods are known, and used for other purposes. Some methods are based on the width of the ECG signal, or the duration of the various components of the ECG signal.

Figure 4:
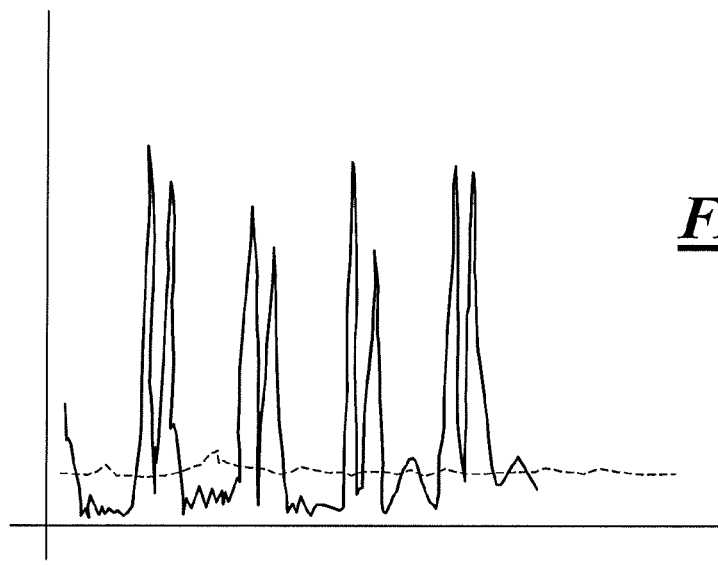
FIG. 4 shows an example of the detection of the signal for a patient with the catheter in a correct position.

A first and a second method will now be discussed with reference to FIG. 4. FIG. 4 illustrates as a solid line the root mean square value of the signal measured between the uppermost and the lowermost electrode of the catheter. This is suitably generated by the sum of all electrode pairs. According to these methods a threshold value may be determined, for example, as a certain level above the base line of the signal. Of course, the threshold value could be determined in any other suitable way, for example, as a constant value. The threshold value is shown as a dashed line in FIG. 4. According to the invention, the periods when the ECG signal is above the thresh-old are considered. Typically, one extra sample is included at the end of each period.

The first and second methods utilize the fact that the width of the period in which the threshold value is exceeded becomes shorter when the catheter is inserted too far in to the esophagus, mainly because the P-wave disappears on the uppermost electrode. According to this embodiment one width is calculated as the sum of the width of the period in which the threshold value is exceeded for the P-wave and for the QRS complex. This may be done by adding the widths for such periods that occur less than a certain distance apart. This distance in time must be selected so that two periods occurring closer in time than this distance should be interpreted as a P-wave and a QRS complex related to the same heart beat. An upper limit for the distance in one implementation of the invention is 48 ms. If two such periods occur closer in time than this distance it can be assumed that they represent a P-wave and a QRS complex, respectively. Preferably, the distance between the periods is excluded when determining the total width of the periods in this case.

Preferably, the widths, or durations, of the periods in which the signal exceeds the threshold value are registered over a number of signal periods and the widths are plotted in a histogram.

Figure 5:
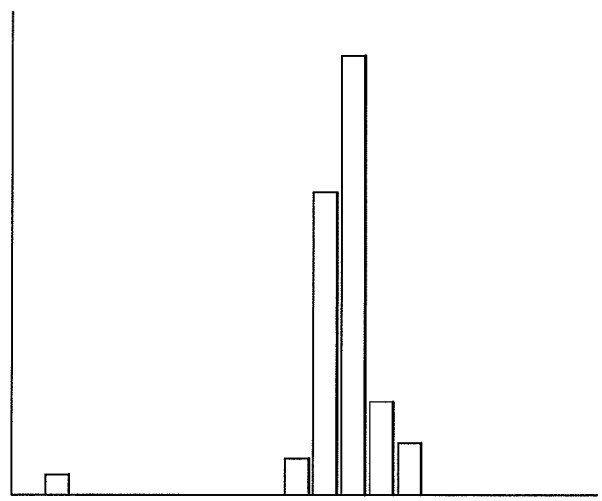
FIG. 5 is a first example of a histogram of periods when the signal exceeds a threshold value.

According to the first method, if any one of the two most frequent widths is above a certain limit value, it is considered to represent a combined P-wave and QRS complex. This value must be chosen such that it is higher than the width the QRS complex alone can reasonably be expected to have. A suitable value in one implementation has been found to be 128 ms. Typically, if any one of the two most frequent widths is 128 ms or more, it is considered to include a P-wave. Such a histogram is shown in FIG. 5.

Figure 6:
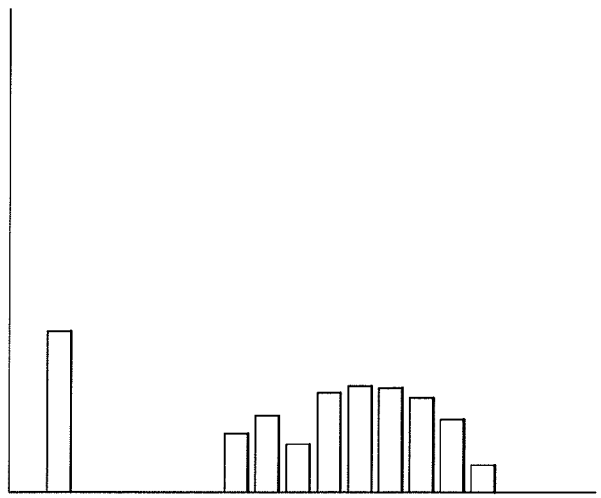
FIG. 6 is a second example of a histogram of periods when the signal exceeds a threshold value.

A second method by which the P-wave can be detected is also based on the length of each period in which the signal exceeds the threshold value, but allows for the possibility that the combined widths of the P-wave and QRS complexes may vary so much that there is not one width that is predominant in the histogram. Therefore, if the fraction of periods having widths between a lower limit value and a higher limit value is higher than, for example, 50% it is considered that this fraction represents a combined P-wave and QRS complex and that therefore a P-wave must be present. Suitable values for the lower and higher limit values have been found in one implementation to be 128 ms and 288 ms, respectively. Such a histogram is shown in FIG. 6. This histogram covers the situation where there may be a relatively strong T wave, which registers as one or more peaks at relatively low values in the histogram and where the sum of the widths of the P-wave and QRS complex varies over a larger number of values. In this case there will not be one single peak, but the sum of all periods having widths in the range of reasonable values for a combined P-wave and QRS complex is such as to indicate that there is a P-wave present.

A third way of detecting the presence of a P-wave is used to handle the situation when the time interval between the P-wave and the QRS complex is longer than the limit time, that is, preferably 48 ms. This may be the case, for example, if the patient suffers from atrioventricular block, or AV block. In this case, the durations of the P-wave and the QRS complex will not be summed and the first two methods will not yield the result of a combined P-wave and QRS complex. The rate r of the periods in which the signal exceeds the threshold is calculated as an average for the last n such periods, according to $$r = \frac{60}{\sum_{i=1}^{n} T(i)/n} \quad (1)$$

A suitable value for n has been found to be 50. T is the time between the start of the periods.

The heart rate is calculated in a manner known in the art. The heart rate, without a potential P-wave, is compared with the rate of periods in which the signal exceeds the threshold value, which includes a P-wave, if present. As explained above, in this case the P-wave and the QRS complex will be considered as two different periods be-cause of the spacing in time between them. If the rate of the periods in which the signal exceeds the threshold value is close to twice the heart rate, for example greater than or equal to 1.8 times the heart rate, it is considered to include a P-wave.

FIG. 7 illustrates a process utilizing all of the different methods discussed above.

In step S51 an ECG component of an EMG signal recorded from an esophageal catheter is determined.

In step S52 the periods in which the ECG component exceeds the threshold value are determined.

In step S53 it is determined if any such periods are closer in time to each other than a certain limit value, for example, 48 ms. If so, the widths of these periods are added to each other.

In step S54 it is determined whether one of the two most frequent widths of the periods is above a certain limit value. If yes, go to step S57; if no, go to step S55. In one embodiment, a suitable limit value is 128 ms. In this case it can be concluded a large fraction of the periods comprise a combined P-wave and QRS complex.

In step S55 it is determined whether a certain fraction of the periods have a width between a lower and an upper limit value. If yes, go to step S57; if no, go to step S56. The fraction may suitably be 50%. In one embodiment, a suitable lower limit value is 128 ms and a suitable upper limit value is 288 ms. In this case, it may be concluded that the periods having a width between the upper and lower limit value comprise a P-wave, while excluding the cases where more of the ECG than the P-wave and the QRS complex are included.

In step S56 the rate of the periods in which the signal exceeds the threshold value is compared to the heart rate and it is determined whether the rate of these periods is close to 2 times the heart rate. If yes, go to step S57; if no go to step S58. A suitable value close to 2 may be 1.8. In this case, it may be concluded that the ECG signal comprises both a P-wave and a QRS complex, which in this case are too far apart in time to be considered as one period. The heart rate may be determined in any suit-able way known in the art.

In step S57 it is concluded that a P-wave is present, so that the esophageal catheter may be considered to be in a good position.

In step S58 it is concluded that no P-wave is present. This may indicate that the esophageal catheter is in the wrong position. It may also have other reasons, for ex-ample, that the patient's P-wave is too weak to be detected. If no P-wave is detected, it should be determined if the catheter is misplaced. This may be done, for example, by checking the NEX measure, as discussed above. A way to verify if the position is ok is to check the synchrony between the measured EMG-signal and the patients breathing efforts registered with flow or pressure. If the positioning is ok, the timing of the myoelectric (EMG) signal attributed to the diaphragm should be correlated with the registered breathing activity of the patient, to check whether or not the two are in phase with each other. If the myoelectric signal indicates that the diaphragm's activity is correlated in time with the patient's breathing activity, this means that the EMG signal is actually representative of the diaphragm's electric activity. Hence, it may be concluded that the position of the catheter is good, but that the patient's ECG signal lacks a P-wave.

The procedure disclosed in FIG. 5 may be performed on all channels simultaneously, or on one or more of the channels. In a preferred embodiment, the procedure is per-formed for the channel received from the uppermost electrode pair only. In this case, if no P-wave is detected on this channel, the procedure could continue with the next (second highest) electrode pair. If no P-wave was detected on this channel either, the procedure could continue with the next electrode pair, and so on. The procedure could also be performed simultaneously for the uppermost 2 or 3 pairs, or any suit-able number of pairs. In any case, if a P-wave is detected on any other channel and not on the uppermost channel, it may be concluded that the catheter has been misplaced. In particular, if a P-wave is detected on any of the lowermost channels and not on the uppermost channels, it may be concluded that the catheter is not inserted far enough into the patient. This may be caused by the catheter sliding out of the patients esophagus, for example, caused by the weight of the cables, movement of the patient, or some other reason.

As the skilled person will understand, the method steps will typically be performed by a computer program arranged to be run in a control unit that is used to control the monitoring of an electrical signal from a catheter inserted into a patient. The catheter is typically an esophageal catheter, and the electrical signal is typically an EMG signal from the patient's diaphragm. The monitoring may be performed, for example, by a ventilator that is used to provide breathing support to the patient, or by a separate monitoring unit. In each case, the device performing the monitoring is con-trolled by the control unit. In this case, the outcome of the method may be used to determine if the esophageal catheter is positioned in a good way so that the EMG signal from the catheter is representative of the patient's breathing activity.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for obtaining an indication of the position of an esophageal catheter inserted into a patient, comprising the steps of:
    obtaining an electrical signal from electrodes carried by an esophageal catheter inserted in the esophagus of a subject;
    supplying said electrical signal to a processor and, in said processor, automatically extracting an ECG component from said electrical signal;
    in said processor, determining a number of periods during which said ECG component exceeds a threshold value;
    in said processor, determining whether a P-wave is present in said ECG component dependent on at least one of a width and a rate of said number of periods; and
    when said P-wave is determined by said processor to be present in said ECG component, emitting an output signal from said processor indicating that the catheter is in a position in the patient for obtaining a correct EMG signal.

2. A method as claimed in claim 1 comprising, in said processor, using said widths of said periods to determine a presence of said P-wave close to a QRS complex.

3. A method as claimed in claim 1 comprising, in said processor, determining that said P-wave is present in said ECG component if one of a two most frequent widths of said period exceeds a predetermined limit value.

4. A method as claimed in claim 1 comprising, in said processor, determining that said P-wave is present in said ECG component if more than a predetermined fraction of said widths of said period are between a lower limit value and an upper limit value.

5. A method as claimed in claim 1 further comprising:
    in said processor, determining a rate of occurrence of said periods;
    detecting a heart rate of the patient and supplying a heart rate signal representing the heart rate to said processor;
    in said processor, comparing said rate of occurrence of said periods to said heart rate; and
    in said processor, determining that a P-wave is present in said ECG component if the rate of occurrence of the periods is approximately twice said heart rate.

6. A method as claimed in claim 1 further comprising, if no P-wave is determined by said processor to be present in said ECG component, automatically identifying and analyzing, in said processor, a further characteristic of the patient indicative of a position of said catheter.

7. A method as claimed in claim 6 wherein said processor analyzes a NEX value as said further characteristic.

8. A non-transitory, computer-readable storage medium loaded into a processor supplied with an electrical signal from a esophageal catheter inserted into a patient, said computer-readable medium being encoded with programming instructions and said programming instructions causing said processor to:
    obtain an electrical signal from electrodes carried by an esophageal catheter inserted in the esophagus of a subject;
    automatically extract an ECG component from said electrical signal;
    determine a number of periods during which said ECG component exceeds a threshold value;
    determine whether a P-wave is present in said ECG component dependent on at least one of a width and a rate of said number of periods; and
    when said P-wave is determined to be present in said ECG component, emit an output signal indicating that the catheter is in a position in the patient for obtaining a correct EMG signal.

9. A non-transitory, computer-readable storage medium as claimed in claim 8 wherein said programming instructions further cause said processor to use said widths of said periods to determine a presence of P-wave close to a QRS complex.

10. A non-transitory, computer-readable storage medium as claimed in claim 8 wherein said programming instructions further cause said processor to determine that a P-wave is present in said ECG component if one of a two most frequent widths of said period exceeds a predetermined limit value.

11. A non-transitory, computer-readable storage medium as claimed in claim 8 wherein said programming instructions further cause said processor to determine that a P-wave is present in said ECG component if more than a predetermined fraction of said widths of said period are between a lower limit value and an upper limit value.

12. A non-transitory, computer-readable storage medium as claimed in claim 8 wherein said programming instructions further cause said processor to:

determine a rate of occurrence of said periods;
detect a heart rate of the patient and supplying a heart rate signal representing the heart rate to said processor;
compare said rate of occurrence of said periods to said heart rate; and
determine that a P-wave is present in said ECG component if the rate of occurrence of the periods is approximately twice said heart rate.

13. A control unit for controlling a ventilator, said control unit comprising:
An input adapted to receive an electrical signal from electrodes carried by an esophageal catheter inserted in the esophagus of a subject;
an output;
a processor that automatically extracts an ECG component from said electrical signal;
said processor being configured to determine a number of periods during which said ECG component exceeds a threshold value;
said processor being configured to determine whether a P-wave is present in said ECG component dependent on at least one of a width and a rate of said number of periods; and
said processor being configured, when said P-wave is determined by said processor to be present in said ECG component, to emit an output signal at said output indicating that the catheter is in a position in the patient for obtaining a correct EMG signal.

14. A ventilator for providing breathing support to a patient, comprising:
a breathing circuit adapted for interaction with a patient to provide breathing support to the patient;
a control unit that controls operation of said breathing circuit, including operation in an EMG-controlled mode;
said control unit having an input adapted to receive an electrical signal from electrodes carried by an esophageal catheter inserted in the esophagus of a subject, and said control unit having an output and a processor connected between said input and output;
said processor being configured to automatically extract an ECG component from said electrical signal;
said processor being configured to determine a number of periods during which said ECG component exceeds a threshold value;
said processor being configured to determine whether a P-wave is present in said ECG component dependent on at least one of a width and a rate of said number of periods; and
said processor being configured, when said P-wave is determined by said processor to be present in said ECG component, to emit an output signal from said processor indicating that the catheter is in a position in the patient for obtaining a correct EMG signal to allow said operation of said breathing circuit in said EMG-controlled mode.

15. A ventilator and esophageal catheter assembly for providing breathing support to a patient, comprising:
an esophageal catheter adapted to be inserted in the esophagus of a subject, said esophageal catheter comprising a plurality of electrodes that generate an electrical signal while the esophageal catheter is in said esophagus;
a breathing circuit adapted for interaction with a patient to provide breathing support to the patient;
a control unit that controls operation of said breathing circuit, including operation in an EMG-controlled mode;
said control unit having an input connected to said esophageal catheter to receive said electrical signal from said electrodes, and said control unit having an output and a processor connected between said input and said output;
said processor being configured to automatically extract an ECG component from said electrical signal;
said processor being configured to determine a number of periods during which said ECG component exceeds a threshold value;
said processor being configured to determine whether a P-wave is present in said ECG component dependent on at least one of a width and a rate of said number of periods; and
said processor being configured, when said P-wave is determined by said processor to be present in said ECG component, to emit an output signal from said processor indicating that the catheter is in a position in the patient for obtaining a correct EMG signal to allow said operation of said breathing circuit in said EMG-controlled mode.

* * * * *